United States Patent [19]

Martin

[11] 4,000,248

[45] Dec. 28, 1976

[54] SYNTHESIS OF ZEOLITES

[75] Inventor: David Eric Martin, Fetcham, England

[73] Assignee: The British Petroleum Company Limited, London, England

[22] Filed: Feb. 21, 1975

[21] Appl. No.: 551,608

[30] Foreign Application Priority Data
Mar. 18, 1974 United Kingdom ............ 11844/74

[52] U.S. Cl. .......................... 423/329; 260/448 C; 423/328; 252/455 Z
[51] Int. Cl.² ....................................... C01B 33/28
[58] Field of Search .......... 423/328, 329, 330, 118; 260/448 C; 253/455 Z

[56] References Cited

UNITED STATES PATENTS

| 3,306,922 | 2/1967 | Barrer et al. .................. 260/448 C |
| 3,702,886 | 11/1972 | Argauer et al. .................... 423/328 |

OTHER PUBLICATIONS

Barrer et al. "Chemical Society Journal" 1964, Part 1, pp. 485–497.
Kerr "Nature", Apr. 16, 1966, vol. 210 pp. 294 and 295.

*Primary Examiner*—Edward J. Meros
*Attorney, Agent, or Firm*—Morgan, Finnegan, Pine, Foley & Lee

[57] ABSTRACT

The zeolite ferrierite is prepared by a process of hydrothermal crystallization in the presence of N-methyl pyridinium hydroxide.

4 Claims, No Drawings

SYNTHESIS OF ZEOLITES

The present invention relates to a method of synthesising zeolites and in particular to a method of synthesising the zeolite ferrierite.

Ferrierite, a rare naturally occurring zeolite, was first reported by R. P. D. Graham (Roy. Soc. Canada, Proc and Trans, 3rd Ser. 12, IV, 185-190). The material was first synthesised by R. M. Barrer and D. T. Marshall in 1964-65 (Jour. Chem. Soc. (1964) 484-497 and the American Mineralogist Vol. 50 April 1965). The method used for this synthesis was hydro thermal crystallisation from an aqueous gel containing a metal hydroxide, aluminum hydroxide gel and a stable silica sol at temperatures of 340° – 400° C under pressures of 2000 – 20,000 psi. Although suitable for small scale laboratory synthesis this method using high temperatures and pressures is not suitable for the preparation of the synthetic zeolite in useful quantities necessary for further testing and research.

It is an object of the present invention to provide a method of synthesising ferrierite employing hydrothermal crystallisation at lower temperatures and pressures than were employed hitherto.

It is also an object of the present invention to provide a method of synthesising samples of ferrierite with higher silica to alumina ratios than were obtained hitherto or have been found in nature.

Accordingly the present invention is a method of synthesising the zeolite ferrierite which comprises hydrothermal crystallisation of the zeolite from an aqueous gel containing an alkali or alkaline earth metal hydroxide, alumina or an alkali metal aluminate, and a colloidal silica sol or an alkali metal silicate and N-methylpyridinium hydroxide in molar ratio $SiO_2/Al_2O_3$ in the range 5:1 to 160:1; $M_2O/SiO_2$ in the range 0.07:1 to 1.8:1; $M_2O/(N\text{-methylpyridinium})_2O$ in the range 0.5:1 to 20:1 Water/$M_2O$ in the range 50:1 to 170:1
wherein $M_2O$ represents $m_2O$ + (N-methylpyridinium)$_2O$ or $mO$ + (N-methylpyridinium)$_2O$ and $m$ represents alkali metal or alkaline earth metal, by heating under auto genous pressure at the elevated temperature.

It has been found that the addition of N-methylpyridinium hydroxide to the aqueous gel substantially reduces the temperature and pressure conditions necessary for the production of the synthetic ferrierite. Thus for example elevated temperatures of about 140° C to 160° C with corresponding pressures of about 40 to 90 psi have been found suitable for the method of the invention.

In one embodiment of the method of the invention the aqueous gel preferably comprises sodium hydroxide and sodium aluminate.

The characteristic d-spacings for the synthetic ferrierite prepared by the method of the invention and those of natural ferrierite are given in the following table.

Table of d-Spacings

| Synthetic Material | | Natural Ferrierite | |
|---|---|---|---|
| d (A) | Relative Intensity | d (A) | Relative Intensity |
| 11.10 | 8 | 11.33 | 20 |
| 9.61 | 100 | 9.61 | 100 |
| 7.19 | 24 | | |
| 7.09 | 37 | 7.00 | 30 |
| 6.73 | 19 | 6.61 | 20 |
| 55.87 | 8 | 5.84 | 50 |
| 5.78 | 9 | | |
| 5.54 | 3 | | |
| 5.06 | 2 | 4.96 | 10 |
| 4.82 | 4 | 4.80 | 10 |
| 4.48 | 9 | 4.58 | 10 |
| 4.06 | 33 | 3.99 | 90 |
| 4.01 | 21 | | |
| 3.92 | 17 | 3.88 | 10 |
| 3.86 | 27 | 3.79 | 20 |
| 3.77 | 11 | 3.69 | 50 |
| 3.73 | 18 | | |
| 3.62 | 39 | 3.54 | 80 |
| 3.55 | 39 | 3.49 | 80 |
| 3.45 | 8 | 3.42 | 20 |
| 3.38 | 9 | 3.31 | 20 |
| | | 3.20 | 10 |
| 3.20 | 15 | 3.15 | 30 |
| 3.10 | 9 | 3.07 | 30 |
| 3.00 | 4 | 2.97 | 30 |
| 2.95 | 4 | 2.90 | 20 |

The synthetic ferrierite may find application as with many other synthetic and natural zeolites for the separation of hydrocarbons by preferential absorption, e.g. separations of p-xylene from mixtures comprising m-xylene, p-xylene, o-xylene and ethyl benzene. For this purpose the synthetic zeolite is preferably activated by calcination at a temperature in the range 500° C to 600° C in a molecular oxygen containing gas e.g. air followed by treatment with a mineral acid i.e. contact with the acid followed by water washing and finally heating at a temperature in the range 500° C to 600° C in a molecular oxygen containing gas e.g. air.

The method of the present invention and the use of the synthetic ferrierite for separating p-xylene by selective adsorption from a mixture containing all the xylene isomers and ethyl benzene is described further with reference to the following Examples.

EXAMPLE 1

218 g Pyridine (2.78 mol) was slowly added to 586 g iodomethane (lb 4.0 mol) in 875 ml toluene. The mixture was stirred overnight at room temperature and the N-methyl pyridinium iodide was collected by filtration, washed with toluene and ether and dried under vacuum at room temperature. The yield was 544 g (2.33 mol). 100 g of this material was dissolved in 250 ml water and converted to the hydroxide solution. The resulting solution was decolourised by passing through activated charcoal and its strength determined by titration with standard acid. This solution of N-methyl pyridinium hydroxide was found to contain 1.21 equivalents of hydroxide ion/kilogram. 24.31 g of this solution was blended with 0.93 g sodium hydroxide, 0.61 g of a commercial sodium aluminate (containing 40.7% $Na_2O$, 52.0% $Al_2O_3$), 42.78 g water, and 44.19 g Ludox HS silica sol. The reaction mixture had the following overall composition:

| | |
|---|---|
| $SiO_2:Al_2O_3$ | 95:1 |
| $M_2O:SiO_2$ | 0.1:1 |
| $H_2O:M_2O$ | 165:1 |
| $Na_2O:(N\text{-methylpyridinium})_2O$ | 1.06:1 |

The resulting gel was heated in an autoclave at 150° C for 6 days. The solid zeolite product was separated by filtration, and its x-ray powder diffraction pattern determined. This showed the product to be a material similar to natural ferrierite in a purity of 70% and when analysed by x-ray fluorescence spectroscopy was found to have a $SiO_2/Al_2O_3$ ratio of 58.7:1.

EXAMPLE 2

A solution of N-methylpyridinium hydroxide containing 0.4 g equivalents of hydroxide ion was prepared as described in Example 1. 35.5 g of this solution was blended with 0.7 g sodium hydroxide, 0.5 g commercial sodium aluminate (containing 26.7% $Na_2O$, 45.0% $Al_2O_3$), 19.9 g of water and 13.3 g Ludox HS silica sol. The resulting gel which had the composition:

| | |
|---|---|
| $SiO_2:Al_2O_3$ | 40:1 |
| $M_2O:SiO_2$ | 0.26:1 |
| $H_2O:M_2O$ | 150:1 |
| (N-methylpyridinium)$_2$O:Na$_2$O | 1.0:1 | was heated in an autoclave for 6 days at 150° C. The solid zeolite product was separated by filtration, calcined in air at 550° C and its x-ray powder diffraction pattern determined, which is set out in the table below. This pattern shows it to be a material similar to natural ferrierite in about 70% purity and when analysed by x-ray fluorescence spectroscopy was found to have a $SiO_2/Al_2O_3$ ratio of 33.6:1.

EXAMPLE 3

A further preparation was performed using N-methylpyridinium iodide instead of the hydroxide. The composition of the mix was determined by taking the same ratios as Example 2 and adding sufficient excess sodium hydroxide to neutralise the iodide. The resulting mix had the composition:

| | |
|---|---|
| $SiO_2:Al_2O_3$ | 39:1 |
| $M_2O:SiO_2$ | 0.385:1 |
| $H_2O:M_2O$ | 100:1 |
| $Na_2O$:(N-methylpyridinium)$_2$O | 2:1 |

This was achieved by dissolving 6.88 g N-methylpyridinium iodide, 2.25 g sodium hydroxide, 0.71 g sodium aluminate (as example 2) in 71.95 g water and blending with 18.22 Ludox HS silica sol. The mixture was heated in an autoclave at 150° C for 6 days, and the solid zeolite product separated by filtration. The pattern showed it to be a material similar to natural ferrierite in about 80% purity and when analyzed by x-ray fluorescence spectroscopy was found to have a $SiO_2/Al_2O_3$ ratio of 28.5:1.

EXAMPLE 4

The material produced in Example 1 was calcined in air for 16 hours at 550° C. It was then refluxed with N-hydrochloric acid for 16 hours, filtered, washed, and the process repeated. The resulting material was finally activated for 16 hours at 550° C in air, and its selectivity for the adsorption of $C_8$ alkyl aromatics determined as follows:

A feed mixture containing 19.0% ethylbenzene, 23.2% p-xylene, 51.3% m-xylene and 6.5% o-xylene was passed over 6.82 g of the above material at a flow rate of 20 ml/hr at 180° C and ambient pressure with a $N_2$ stream at 60 ml/min. The feed mixture was passed over the adsorbent until the effluent from the adsorber had the same composition as the feed; this was discontinued and the adsorbent was purged with $N_2$ at 100 ml/min for 5 minutes. The adsorbate was then desorbed by passing toluene at 30 ml/min for 17 minutes. The total amount of $C_8$ aromatics desorbed was equal to 1.7% of the adsorbent weight. The composition of the desorbed $C_8$ aromatics was 27.3% ethylbenzene, 58.3% p-xylene, 12.8% m-xylene and 1.6% o-xylene. These results show a selective adsorption of p-xylene from a mixture of $C_8$ aromatics.

I claim:

1. A method of synthesising the zeolite ferrierite which comprises hydrothermal crystallisation of the zeolite from an aqueous gel prepared from (1) an agent selected from the group consisting of an alkali metal hydroxide and an alkaline earth metal hydroxide, (2) an agent selected from the group consisting of alumina and an alkali metal aluminate, (3) an agent selected from the group consisting of a colloidal silica sol and an alkali metal silicate, and (4) N-methyl pyridinium hydroxide in molar ratio
$SiO_2/Al_2O_3$ in the range 5:1 to 160:1; $M_2O/SiO_2$ in the range 0.07 to 1.8:1; $M_2O/$(N-methylpyridinium)$_2O$ in the range 0.5:1 to 20:1; Water/$M_2O$ in the range 50:1 to 170:1
wherein $M_2O$ represents compositions selected from the group consisting of $m_2O +$ (N-methylpyridinium)$_2O$ and $mO +$ (N-methylpyridinium)$_2O$ and $m$ represents a metal selected from the group consisting of an alkali metal and alkaline earth metal, by heating under pressures in the range of 40 to 90 psi. at a temperature in the range of 140° to 160° C.

2. A method as claimed in claim 1 wherein the aqueous gel is prepared from sodium hydroxide, sodium aluminate, silica sol and N-methyl pyridinium hydroxide.

3. A method as claimed in claim 1 wherein the zeolite produced is calcined by heating to a temperature in the range 500° C. to 600° C. in a molecular oxygen containing gas and is thereafter treated with a mineral acid, washed with water, and finally reclaimed at a temperature in the range of 500° C. to 600° C. in a molecular oxygen contaning gas.

4. A method as claimed in claim 3 wherein the mineral acid is hydrochloric acid.

* * * * *